(12) United States Patent
Tang

(10) Patent No.: US 9,433,217 B2
(45) Date of Patent: Sep. 6, 2016

(54) METHODS AND COMPOSITIONS FOR INTRODUCTION OF EXOGENOUS DSRNA INTO PLANT CELLS

(75) Inventor: Guo-Qing Tang, Durham, NC (US)

(73) Assignee: Syngenta Participations AG, Basel (CH)

( * ) Notice: Subject to any disclaimer, the term of this patent is extended or adjusted under 35 U.S.C. 154(b) by 395 days.

(21) Appl. No.: 13/585,947

(22) Filed: Aug. 15, 2012

(65) Prior Publication Data
US 2013/0047298 A1    Feb. 21, 2013

Related U.S. Application Data

(60) Provisional application No. 61/523,877, filed on Aug. 16, 2011.

(51) Int. Cl.
*A01N 57/16*    (2006.01)
*C12N 15/82*    (2006.01)

(52) U.S. Cl.
CPC ............ *A01N 57/16* (2013.01); *C12N 15/8206* (2013.01); *C12N 15/8218* (2013.01)

(58) Field of Classification Search
CPC .......... C12N 15/8206; C12N 15/8218; A01N 57/16
See application file for complete search history.

(56) References Cited

U.S. PATENT DOCUMENTS

| 6,271,176 B1 * | 8/2001 | Kamuro | A01N 37/42 504/140 |
| 2008/0214443 A1 * | 9/2008 | Baum | C12N 15/8286 514/1.1 |

FOREIGN PATENT DOCUMENTS

| CN | 101914540 | * 12/2010 | A01H 5/00 |
| CN | 101914540 A | * 12/2010 | |
| WO | WO2011112570 A1 | 9/2011 | |

OTHER PUBLICATIONS

Vidya et al (1998) Phytochemistry 48: 927-930.*
Saitoh et al (2002) Genes Genet. Syst. 77: 335-340.*
CN101914540A, machine translation: www.google.com/patents, 2014.*
Vardhini, B. Vidya, and S. Seeta Ram Rao. "Effect of brassinosteroids on growth, metabolite content and yield of Arachis hypogaea." Phytochemistry 48.6 (1998): 927-930.*
Saitoh, Hiromasa, and Ryohei Terauchi. "Virus-induced silencing of FtsH gene in Nicotiana benthmiana causes a striking bleached leaf phenotype." Genes & genetic systems 77.5 (2002): 335-340.*
International Search Report and Written Opinion, International Application No. PCT/US12/50687, dated Nov. 5, 2012.
Hunter, Wayne et al. Large-scale field application of RNAi technology reducing Israeli acute paralysis virus disease in honey bees (*Apis meilifera*, Hymenoptera: Apidae). PLoS Pathogens Dec. 2010 vol. 6 No. 12 e1001160, pp. 1-10.
Gan et al. Bacteriaily expressed dsRNA protects maize against SCMV infecton. Plant Cell Rep Nov. 2010 vol. 29 No. 11 pp. 1261-1268.
Tenllado et al. Crude extracts of bacterially expressed dsRNA can be used to protect plants against virus infections. BMC Biotechnol Mar. 20, 2003 vol. 3 No. 3, pp. 1-11.
Saitoh et al. Virus-induced sitenoing of FtsH gene in Nicotiana benthmiana causes a striking bleached leaf phenotype. Genes Genet Syst Oct. 2002 vol. 77 No. 5, pp. 335-340.
Bajguz et al. The chemical characteristic and distribution of brassinosteroids in plants. Phytochemistry 62 (2003), pp. 1027-1046.
Saleh et al., Nature Cell Biology, 2006, 8, 6, 793-802.
Ulylla et al., The Journal of Biological Chemistry, 2006, 281, 20, 14370-14375.
McEwan et al., Molecular Cell, 2012, 47, 5, 746-754.
Irani et al., Nature Chemical Biology, 2012, 8, 583-589.
Vardhini et al., Phytochemistry,1998, 48, 6, 927-930.

* cited by examiner

*Primary Examiner* — Russell Kallis
*Assistant Examiner* — Weihua Fan
(74) *Attorney, Agent, or Firm* — Joshua L. Price

(57) ABSTRACT

This invention provides a method to silence an endogenous target gene expression in plants by applying a specific dsRNA onto the exterior surface of a plant. Application, such as by spraying or brushing a plant with dsRNA is done without wounding the plant tissue and cells such as by mechanical-type wounding, particle bombardment or mechanical infection with viral vectors. The present invention enables the regulation of gene expression in plants. In some embodiments of the invention, the dsRNA is directed to an essential gene of a plant pathogen or pest, whereby the pathogen and/or pest damage is controlled, resulting in desired agronomic performance.

7 Claims, No Drawings

SEQUENCE LISTING

<160> NUMBER OF SEQ ID NOS: 12

<210> SEQ ID NO 1
<211> LENGTH: 600
<212> TYPE: DNA
<213> ORGANISM: Artificial Sequence
<220> FEATURE:
<223> OTHER INFORMATION: Synthetic Florescent protein

<400> SEQUENCE: 1

| | | | | | |
|---|---|---|---|---|---|
| agggctgcgt | ggacggccac | aagttcgtga | tcaccggcga | gggcatcggc | tacccottca | 60 |
| agggcaagca | ggccatcaac | ctgtgcgtgg | tggagggcgg | ccccttgccc | ttcgccgagg | 120 |
| acatcttgtc | cgccgccttc | atgtacggca | accgcgtgtt | caccgagtac | ccccaggaca | 180 |
| tcgtcgacta | cttcaagaac | tcctgccccg | ccggctacac | ctgggaccgc | tccttcctgt | 240 |
| tcgaggacgg | cgccgtgtgc | atctgcaacg | ccgacatcac | cgtgagcgtg | gaggagaact | 300 |
| gcatgtacca | cgagtccaag | ttctacgcgc | tgaacttccc | cgccgacggc | cccgtgatga | 360 |
| agaagatgac | cgacaactgg | gagccctcct | gcgagaagat | catccccgtg | cccaagcagg | 420 |
| gcatcttgaa | gggcgacgtg | agcatgtacc | tgctgctgaa | ggacggtggc | cgcttgcgct | 480 |
| gccagttcga | caccgtgtac | aaggccaagt | ccgtgccccg | caagatgccc | gactggcact | 540 |
| tcatccagca | caagctgacc | cgcgaggacc | gcagcgacgc | caagaaccag | aagtggcacc | 600 |

<210> SEQ ID NO 2
<211> LENGTH: 1071
<212> TYPE: DNA
<213> ORGANISM: Zea mays

<400> SEQUENCE: 2

| | | | | | |
|---|---|---|---|---|---|
| atggcctgcc | tcaccgacct | cgtcaacctc | aacctctcgg | acaacaccga | gaagatcatc | 60 |
| gcggaataca | tatggatcgg | tggatctggc | atggatctca | ggagcaaagc | aaggaccctc | 120 |
| tccggcccgg | tgaccgatcc | cagcaagctg | cccaagtgga | actacgacgg | ctccagcacg | 180 |
| ggccaggccc | ccggcgagga | cagcgaggtc | atcttgtacc | cgcaggccat | cttcaaggac | 240 |
| ccattcagga | ggggcaacaa | catccttgtg | atgtgcgatt | gctacacccc | agccggcgag | 300 |
| ccaatcccca | ccaacaagag | gtacaacgcc | gccaagatct | tcagcagccc | tgaggtcgcc | 360 |
| gccgaggagc | cgtggtatgg | tattgagcag | gagtacaccc | tcctccagaa | ggacaccaac | 420 |
| tggcccettg | ggtggcccat | cggtggcttc | cccggccctc | aggtccttta | ctactgtgga | 480 |
| atcggcgccg | aaaagtcgtt | cggccgcgac | atcgtggacg | cccactacaa | ggcctgcttg | 540 |
| tatgcgggca | tcaacatcag | tggcatcaac | ggggaggtga | tgccaggggca | gtgggagttc | 600 |
| caagtcgggc | cttccgtggg | tatttcttca | ggcgaccagg | tctggtcgc | tgctacatt | 660 |
| cttgagagga | tcacggagat | cgccggtgtg | gtggtgacgt | tcgacccgaa | gccgatcccg | 720 |
| ggcgactgga | acggcgccgg | cgcgcacacc | aactacagca | cggagtcgat | gaggaaggag | 780 |
| ggcgggtacg | aggtgatcaa | gcggccatc | gagaagctga | agctgcggca | cagggagcac | 840 |
| atcgcggcct | acggcgaggg | caacgagcgc | cggctcaccg | gcaggcacga | gaccgccgac | 900 |
| atcaacacgt | tcagctgggg | cgtggccaac | cgcggcgcgt | cggtgcgcgt | gggccgggag | 960 |
| acggagcaga | acggcaaggg | ctacttcgag | gaccgccgcc | cggcgtccaa | catggacccc | 1020 |
| tacgtggtca | cctccatgat | cgccgagacc | accatcatct | ggaagccctg | a | 1071 |

<210> SEQ ID NO 3
<211> LENGTH: 395

```
<212> TYPE: DNA
<213> ORGANISM: Nicotiana tabacum

<400> SEQUENCE: 3
caaatggcag ttgcacttgg tgaaagggtt gctgaggagg ttattttgg acaagataac      60
gtaacaactg gggcatctaa cgatttcatg caagtttcac gagtggcaag gcagatggtt    120
gagagattag ggttcagcaa aaagattgga caagttgcca ttggaggagg tggaggaaat    180
cctttcctag tcaacagat gtcaacccag aaagactact ccatggctac agccgatgtg     240
gttgatgctg aagtaaggga attggttgaa agagcatatg aaagggcaac agagattatc    300
acaacacaca ttgacatcct acacaagctt gctcagctgt tgatagagaa agaaactgtt    360
gatggtgaag agttcatgag cctttttcatc gatgg                              395

<210> SEQ ID NO 4
<211> LENGTH: 1761
<212> TYPE: DNA
<213> ORGANISM: Nicotiana tabacum

<400> SEQUENCE: 4
atgccccaaa tcggacttgt atctgctgtt aatttgagag tccaaggtaa ttcagcttat      60
ctttggagct cgaggtcttc gttgggaact gaaagtcaag atgtttgctt gcaaaggaat    120
ttgttatgtt ttggtagtag cgactccatg gggcataagt taaggattcg tactccaagt    180
gccacgaccc gaagattgac aaaggacttt aatcctttaa aggtagtctg cattgattat    240
ccaagaccag agctagacaa tacagttaac tatttggagg cggcgttatt atcatcatcg    300
tttcgtactt cctcacgccc aactaaacca ttggagattg ttattgctgg tgcaggtttg    360
ggtggtttgt ctacagcaaa atatctggca gatgctggtc acaaaccgat attgctggag    420
gcaagagatg tcctaggtgg gaaggtagct gcatggaaag atgatgatgg agattggtac    480
gagactgggt tgcacatatt ctttggggct acccaaaata tgcagaacct gtttggagaa    540
ctagggattg atgatcggtt gcagtggaag gaacattcaa tgatatttgc gatgcctaac    600
aagccagggg agttcagccg ctttgatttt cctgaagctc ttcctgcgcc attaaatgga    660
atttttggcca tactaaagaa caacgaaatg cttacgtggc ccgagaaagt caaatttgct    720
attggactct tgccagcaat gcttggaggg caatcttatg ttgaagctca agacggttta    780
agtgttaagg actggatgag aaagcaaggt gtgcctgata gggtgacaga tgaggtgttc    840
attgccatgt caaaggcact taacttcata aaccctgacg agctttcgat gcagtgcatt    900
ttgattgctt tgaacagatt tcttcaggag aaacatggtt caaaaatggc cttttttagat    960
ggtaaccctc ctgagagact ttgcatgccg attgtggaac atattgagtc aaaaggtggc    1020
caagtcagac taaactcacg aataaaaaag atcgagctga atgaggatgg aagtgtcaaa    1080
tgttttatac tgaataatgg cagtacaatt aaaggagatg cttttgtgtt tgccactcca    1140
gtggatatct tgaagcttct tttgcctgaa gactggaaag agatcccata tttccaaaag    1200
ttggagaagc tagtgggagt tcctgtgata aatgtccata tatggtttga cagaaaactg    1260
aagaacacat ctgataatct gctcttcagc agaagcccgt tgctcagtgt gtacgctgac    1320
atgtctgtta catgtaagga atattacaac cccaatcagt ctatgttgga attggtattt    1380
gcacccgcag aagagtggat aaatcgtagt gactcagaaa ttattgatgc tacaatgaag    1440
gaactagcga agcttttccc tgatgaaatt tcggcagatc agagcaaagc aaaaatattg    1500
aagtatcatg ttgtcaaaac cccaaggtct gtttataaaa ctgtgccagg ttgtgaaccc    1560
```

| | | |
|---|---|---|
| tgtcggccct tgcaaagatc ccctatagag ggttttttatt tagctggtga ctacacgaaa | 1620 | |
| cagaagtact tggcttcaat ggaaggtgct gtcttatcag gaaagctttg tgcacaagct | 1680 | |
| attgtacagg attacgagtt acttcttggc cggagccaga agatgttggc agaagcaagc | 1740 | |
| gtagttagca tagtgaacta a | 1761 | |

<210> SEQ ID NO 5
<211> LENGTH: 600
<212> TYPE: RNA
<213> ORGANISM: Zea mays
<220> FEATURE:
<221> NAME/KEY: Sense strand of SEQIDNO1
<222> LOCATION: (1)..(600)

<400> SEQUENCE: 5

| | | |
|---|---|---|
| agggcugcgu ggacggccac aaguucguga ucaccggcga gggcaucggc uaccccuuca | 60 | |
| agggcaagca ggccaucaac cugugcgugg uggagggcgg ccccuugccc uucgccgagg | 120 | |
| acaucuuguc cgccgccuuc auguacggca accgcguguu caccgaguac ccccaggaca | 180 | |
| ucgucgacua cuucaagaac uccugccccg ccggcuacac cugggaccgc uccuuccugu | 240 | |
| ucgaggacgg cgccgugugc aucugcaacg ccgacaucac cgugagcgug gaggagaacu | 300 | |
| gcauguacca cgaguccaag uucuacggcg ugaacuuccc cgccgacggc cccgugauga | 360 | |
| agaagaugac cgacaacugg gagccccccu gcgagaagau caucccgug cccaagcagg | 420 | |
| gcaucuugaa gggcgacgug agcaugacc ugcugcugaa ggacgguggc cgcuugcgcu | 480 | |
| gccaguucga caccguguac aaggccaagu ccgugcccg caagaugccc gacuggcacu | 540 | |
| ucauccagca caagcugacc cgcgaggacc gcagcgacgc caagaaccag aaguggcacc | 600 | |

<210> SEQ ID NO 6
<211> LENGTH: 600
<212> TYPE: RNA
<213> ORGANISM: Zea mays
<220> FEATURE:
<221> NAME/KEY: Complement of SEQIDNO 5
<222> LOCATION: (1)..(600)

<400> SEQUENCE: 6

| | | |
|---|---|---|
| ucccgacgca ccugccggug uucaagcacu aguggccgcu cccguagccg auggggaagu | 60 | |
| ucccguucgu ccgguaguug gacacgcacc accucccgcc ggggaacggg aagcggcucc | 120 | |
| uguagaacag gcggcggaag uacaugccgu uggcgcacaa guggcucaug gggguccugu | 180 | |
| agcagcugau gaaguucuug gacgggggc ggccgaugug gacccuggcg aggaaggaca | 240 | |
| agcuccugcc gcggcacacg uagacguugc ggcuguagug gcacucgcac cuccucuuga | 300 | |
| cguacauggu gcucagguuc aagaugccgc acuugaaggg gcggcugccg gggcacuacu | 360 | |
| ucuucuacug gcuguugacc cucgggagga cgcucuucua guaggggcac ggguucguc | 420 | |
| cguagaacuu cccgcugcac ucguacaugg acgacgacuu ccugccaccg gcgaacgcga | 480 | |
| cggucaagcu guggcacaug uuccgguuca ggcacggggc guucuacggg cugaccguga | 540 | |
| aguaggucgu guucgacugg gcgcuccugg cgucgcugcg guucuugguc uucaccgugg | 600 | |

<210> SEQ ID NO 7
<211> LENGTH: 1071
<212> TYPE: RNA
<213> ORGANISM: Zea mays
<220> FEATURE:
<221> NAME/KEY: Sense strand of SEQIDINO2
<222> LOCATION: (1)..(1071)

```
<400> SEQUENCE: 7
auggccugcc ucaccgaccu cgucaaccuc aaccucucgg acaacaccga gaagaucauc      60
gcggaauaca uauggaucgg uggaucuggc auggaucuca ggagcaaagc aaggacccuc     120
uccggcccgg ugaccgaucc cagcaagcug cccaagugga acuacgacgg uccagcacg      180
ggccaggccc ccggcgagga cagcgagguc aucuuguacc cgcaggccau cuucaaggac    240
ccauucagga ggggcaacaa cauccuugug augugcgauu gcuacacccc agccggcgag    300
ccaaucccca ccaacaagag guacaacgcc gccaagaucu ucagcagccc ugaggucgcc   360
gccgaggagc cgugguaugg uauugagcag gaguacaccc uccuccagaa ggacaccaac   420
uggcccuug ggugcccau cgguggcuuc cccggcccuc aggguccuua cuacugugga    480
aucggcgccg aaaagucguu cggccgcgac aucguggacg cccacuacaa ggccugcuug   540
uaugcgggca ucaacaucag uggcaucaac ggggaggua ugcagggca gugggaguuc   600
caagucgggc cuccguggg uauuucuuca ggcgaccagg ucugggucgc ucgcuacauu   660
cuugagagga ucacggagau cgccggugug gugugacgu cgacccgaa gccgaucccg   720
ggcgacugga acggcgccgg cgcgcacacc aacuacagca cggagucgau gaggaaggag   780
ggcggguacg aggugaucaa ggcggccauc gagaagcuga agcugcggca cagggagcac   840
aucgcggccu acggcgaggg caacgagcgc cggcucaccg gcaggcacga gaccgccgac   900
aucaacacgu ucagcugggg cguggccaac cgcggcgcgu cggugcgcgu gggccgggag   960
acggagcaga acggcaaggg cuacuucgag gaccgccgcc cggcguccaa cauggacccc  1020
uacguggca ccuccaugau cgccgagacc accaucaucu ggaagcccug a           1071

<210> SEQ ID NO 8
<211> LENGTH: 1071
<212> TYPE: RNA
<213> ORGANISM: Zea mays
<220> FEATURE:
<221> NAME/KEY: Complement of SEQIDNO7
<222> LOCATION: (1)..(1071)

<400> SEQUENCE: 8
uaccggacgg aguggcugga gcaguuggag uuggagagcc uguuguggcu cuucuaguag      60
cgccuuaugu auaccuagcc accuagaccg uaccuagagu ccucguuucg uuccugggag    120
aggccgggcc acuggcuagg gucguucgac ggguucaccu ugaugcugcc gaggucgugc    180
ccggucgggg ggccgcuccu gucgcuccag uagaacaugg cguccgguu aaguuccug    240
gguaagnccu ccccguuguu uaggaacac uacgcuaa cgaugugggg ucggccgcuc    300
gguuagnggu gguuguucuc caugnugcgg cgguucuaga agucgucggg acuccagcgg  360
cggcuccucg gcaccauacc auaacucguc ucaugnggg aggaggcuuu ccuguggung   420
accggggaac ccaccgggua gccaccgaag gggccgggag ucccaggaau gaugacaccu   480
uagccgcggc uuuucagcaa gccggcgcug uagcaccugc gggugauguu ccggacgaac  540
auacgcccgu aguuguaguc accguaguug ccccuccacu acggucccgu cacccucaag    600
guucagcccg gaaggcaccc auaaagaagu ccgcugguc agaccagcg agcgauguaa    660
gaacucuccu agugccucua gcggccacac caccacugca agcugggcuu cggcuagggc   720
ccgcugaccu ugccgcggcc gcgcugugg uugaugucgu gccucagcua cuccuuccuc   780
ccgcccaugc uccacuaguu ccgcggguag ucuucgacu ucgacgccgu gcccucgug    840
uagcgccgga ugccgcuccc guugcucgcg gccgagugcc cguccgugcu cuggcggcug    900
```

| | |
|---|---|
| uaguugugca agucgacccc gcaccgguug gcgccgcgca gccacgcgca cccggcccuc | 960 |
| ugccucgucu ugccguuccc gaugaagcuc cuggcggcgg gccgcagguu guaccugggg | 1020 |
| augcaccagu ggagguacua gcggcucugg ugguaguaga ccuucgggac u | 1071 |

```
<210> SEQ ID NO 9
<211> LENGTH: 395
<212> TYPE: RNA
<213> ORGANISM: Nicotiana tabacum
<220> FEATURE:
<221> NAME/KEY: Sense strand of SEQIDNO3
<222> LOCATION: (1)..(395)

<400> SEQUENCE: 9
```

| | |
|---|---|
| caaauggcag uugcacuugg ugaaagggu gcugaggagg uuauuuugg acaagauaac | 60 |
| guaacaacug gggcaucuaa cgauuucaug caaguuucac gaguggcaag gcagauggu | 120 |
| gagagauuag gguucagcaa aaagauugga caaguugcca uggaggagg uggaggaaau | 180 |
| ccuuuccuag gucaacagau gucaacccag aaagacuacu ccauggcuac agccgaugug | 240 |
| guugaugcug aaguaaggga auugguugaa agagcauaug aaagggcaac agagauuauc | 300 |
| acaacacaca uugacauccu acacaagcuu gcucagcugu gauagagaa agaaacuguu | 360 |
| gauggugaag aguucaugag ccuuucauc gaugg | 395 |

```
<210> SEQ ID NO 10
<211> LENGTH: 395
<212> TYPE: RNA
<213> ORGANISM: Nicotiana tabacum
<220> FEATURE:
<221> NAME/KEY: Complement of SEQIDNO9
<222> LOCATION: (1)..(395)

<400> SEQUENCE: 10
```

| | |
|---|---|
| guuuaccguc aacgugaacc acuuucccaa cgacuccucc aauaaaaacc uguucuauug | 60 |
| cauuguugac cccguagauu gcuaaaguac guucaaagug cucaccguuc cgucuaccaa | 120 |
| cucucuaauc ccaagucguu uucuaaccu guucaacggu aaccuccucc accuccuuua | 180 |
| ggaaaggauc caguugucua caguggguc uuucugauga gguaccgaug ucggcuacac | 240 |
| caacuacgac uucauucccu uaaccaacuu ucucguauac uuucccguug ucucuaauag | 300 |
| uguugugugu aacuguagga ugugucgaa cgagucgaca acuaucucuu cuuugacaa | 360 |
| cuaccacuuc ucaaguacuc ggaaaaguag cuacc | 395 |

```
<210> SEQ ID NO 11
<211> LENGTH: 1761
<212> TYPE: RNA
<213> ORGANISM: Nicotiana tabacum
<220> FEATURE:
<221> NAME/KEY: Sense strand of SEQIDNO4
<222> LOCATION: (1)..(1761)

<400> SEQUENCE: 11
```

| | |
|---|---|
| augccccaaa ucggacuugu aucgcuguu aauuugagag uccaagguaa uucagcuuau | 60 |
| cuuuggagcu cgaggucuuc guggggaacu gaaagucaag auguugcuu gcaaaggaau | 120 |
| uuguuauguu uggguaguag cgacuccaug gggcauaagu uaaggauucg uacuccaagu | 180 |
| gccacgaccc gaagauugac aaaggacuuu aauccuuuaa agguagucug cauugauuau | 240 |
| ccaagaccag agcuagacaa uacaguuaac uauuuggagg cggcguuauu aucaucaucg | 300 |
| uuucguacuu cccuacgccc aacuaaaacca uuggagauug uuauugcugg ugcagguuug | 360 |

| | |
|---|---|
| ggugguuugu cuacagcaaa auaucuggca gaugcugguc acaaaccgau auugcuggag | 420 |
| gcaagagaug uccuaggugg aagguagcu caugaaag augaugaugg agauugguac | 480 |
| gagacuggu ugcacauauu cuuuggggcu acccaaaua ugcagaaccu guuggagaa | 540 |
| cuagggauu augaucgguu gcaguggaag gaacauucaa ugauauuugc gaugccuaac | 600 |
| aagccagggg aguucagccg cuugauuuu ccugaagcuc uuccugcgcc auuaaaugga | 660 |
| auuuggcca acuaaagaa caacgaaaug cuuacguggc ccgagaaagu caaauuugcu | 720 |
| auuggacucu ugccagcaau gcuuggaggg caaucuuaug uugaagcuca agacgguuua | 780 |
| aguguuaagg acuggaugag aaagcaaggu gugccugaua ggugacaga ugagguguuc | 840 |
| auugccaugu caaaggcacu uaacuucaua aacccugacg agcuuucgau gcagugcauu | 900 |
| uugauugcuu ugaacagauu ucuucaggag aaacaugguu caaaaauggc cuuuuuagau | 960 |
| gguaacccuc cugagagacu uugcaugccg auuguggaac auauugaguc aaaaggguggc | 1020 |
| caagucagac uaaacucacg aauaaaaag aucgagcuga augaggaugg aagugucaaa | 1080 |
| uguuuuauac ugaauaaugg caguacaauu aaaggagaug cuuuugnguu ugccacucca | 1140 |
| gugauaucu ugaagcuucu uuugccugaa gacuggaaag agaucccaua uuccaaaag | 1200 |
| uuggagaagc uagggagu uccugugauu aauguccaua uagguuuga cagaaaacug | 1260 |
| aagaacacau cugauaaucu gcuucucagc agaagcccgu ugcucagugu guacgcugac | 1320 |
| augucuguua caugaagga auauuacaac cccaaucagu cuauguugga auuggauu | 1380 |
| gcacccgcag aagaguggau aaaucguagu gacucagaaa uuauugaugc uacaaugaag | 1440 |
| gaacuagcga agcuuuuccc ugaugaaauu ucggcagauc agagcaaagc aaaaauauug | 1500 |
| aaguaucaug uugucaaaac cccaaggucu guuuauaaaa cugugccagg uugugaaccc | 1560 |
| ugucggcccu ugcaaagauc cccuauagag gguuuuauu uagcggugu cuacacgaaa | 1620 |
| cagaaguacu uggcuucaau ggaaggugcu gucuuaucag gaaagcuuug ugcacaagcu | 1680 |
| auugaucagg auuacgaguu acuucuuggc cggagccaga agauguuggc agaagcaagc | 1740 |
| guaguuagca uagugaacua a | 1761 |

<210> SEQ ID NO 12
<211> LENGTH: 1761
<212> TYPE: RNA
<213> ORGANISM: Nicotiana tabacum
<220> FEATURE:
<221> NAME/KEY: Complement of SEQIDNO11
<222> LOCATION: (1)..(1761)

<400> SEQUENCE: 12

| | |
|---|---|
| uacggguuu agccugaaca uagacgacaa uuaaacucuc agguuccauu aagucgaaua | 60 |
| gaaaccucga gcccagaag caaccccuuga cuucaguuc acaaacgaa cguuccuua | 120 |
| aacaauacaa aaccaucauc gcugagguac cccguauuca auuccuaagc augagguuca | 180 |
| cggugcuggg cuucuaacug uuccugaaa uuaggaaauu uccaucagac guaacuaaua | 240 |
| gguucugguc ucgaucuguu augucaauug auaaaccucc gccgcaauaa uaguaguagc | 300 |
| aaagcaugaa ggagugcggg uugauuuggu aaccucuaac aauaacgacc acguccaaac | 360 |
| ccaccaaaca gaugucguuu auagaccgu cuacgaccag guuuggcua uaacgaccuc | 420 |
| cguucucuac aggauccacc cuuccaucga cguaccuuuc uacuacuacc ucuaaccaug | 480 |
| cucugacccca acguguauaa gaaacccga auggguuuau acgucuugga caaaccucuu | 540 |
| gaucccuaac uacuagccaa cgucaccuuc cuuguaaguu acuauaaacg cuacggauug | 600 |

```
uucggucccc ucaagucggc gaaacuaaaa ggacuucgag aaggacgcgg uaauuuaccu    660
uaaaaccggu augauuucuu guugcuuuac gaaugcaccg ggcucuuuca guuuaaacga    720
uaaccugaga acggucguua cgaaccuccc guuagaauac aacuucgagu ucugccaaau    780
ucacaauucc ugaccuacuc uuucguucca cacggacuau cccacugucu acuccacaag    840
uaacgguaca guuuccguga auugaaguau uugggacugc ucgaaagcua cgucacguaa    900
aacuaacgaa acuugucuaa agaaguccuc uuuguaccaa guuuuuaccg gaaaaaucua    960
ccauugggag gacucucuga aacguacggc uaacaccuug uauaacucag uuuuccaccg   1020
guucagucug auuugagugc uuauuuuuuc uagcucgacu uacuccuacc uucacaguuu   1080
acaaaauaug acuuauuacc gucauguaaa uuuccucuac gaaaacacaa acggugaggu   1140
caccuauaga acuucgaaga aaacggacuu cugaccuuuc ucuaggguau aaagguuuuc   1200
aaccucuucg aucacccuca aggacacuau uuacagguau auaccaaacu gucuuuugac   1260
uucuugugua gacuauuaga cgagaagucg ucuucgggca acgagucaca caugcgacug   1320
uacagacaau guacauuccu uauaauguug ggguuaguca gauacaaccu uaaccauaaa   1380
cgugggcguc uucucaccua uuuagcauca cugagucuuu aauaacuacg auguuacuuc   1440
cuugaucgcu ucgaaaaggg acuacuuuaa agccgucuag ucucguuucg uuuuuauaac   1500
uucauaguac aacaguuuug ggguuccaga caaauauuuu gacacggucc aacacuuggg   1560
acagccggga acguuucuag gggauaucuc ccaaaaauaa aucgaccacu gaugugcuuu   1620
gucuucauga accgaaguua ccuuccacga cagaauaguc cuuucgaaac acguguucga   1680
uaacaugucc uaaugcucaa ugaagaaccg gccucggucu ucuacaaccg ucuucguucg   1740
caucaaucgu aucacuugau u                                            1761
```

METHODS AND COMPOSITIONS FOR INTRODUCTION OF EXOGENOUS DSRNA INTO PLANT CELLS

REFERENCE TO RELATED APPLICATIONS

This application claims the priority benefit under Title 35, United States Code 119(e) of U.S. Provisional Patent Application No. 61/523,877 filed Aug. 16, 2011.

STATEMENT REGARDING ELECTRONIC SUBMISSION OF A SEQUENCE LISTING

A Sequence Listing in ASCII test format, submitted under 37 C.F.R. 1.821, entitled "73311_US_NP1_15Aug2012_ O_Application_NR_SequenceListing.txt", 5701 bytes in size, generated on Aug. 14, 2012 and filed via EFS-Web is provided in lieu of a paper copy. This sequence listing is hereby incorporated by reference into the specification for its disclosure.

FIELD OF THE INVENTION

The invention relates to RNA methods and compositions that include RNA formulations that are applied to external plant parts, preferably the leaves, wherein the dsRNA is assimilated into the plant cells.

BACKGROUND

Many food sources are produced by crop plants. Environmental conditions such as drought and heat often adversely affect crop growth and yield. Pest pressure may also have a substantial negative impact. Consequently, plants that are capable of withstanding environmental stresses and/or pest challenge are desirable. Plants tolerant or resistant to abiotic and biotic stresses can be obtained by selective breeding or through genetic modification. RNA interference 15 (RNAi) can be used to produce genetically modified plants that are tolerant or resistant to abiotic and biotic stresses.

In the past decade, RNAi has been described and characterized in organisms as diverse as plants, fungi, nematodes, hydra, and humans. Zamore and Haley (2005) *Science* 309, 1519-24. RNA interference in plants is commonly referred to as post-transcriptional gene silencing or RNA silencing and is referred to as quelling in fungi. The process of post-transcriptional gene silencing is thought to be an evolutionarily conserved cellular defense mechanism used to prevent the expression of foreign genes and is commonly shared by diverse flora and phyla. Fire (1999) *Trends Genet.* 15, 358-363.

RNA interference occurs when an organism recognizes double-stranded RNA molecules and hydrolyzes them. The resulting hydrolysis products are small RNA fragments of 19-24 nucleotides in length, called small interfering RNAs (siRNAs) or microRNAs (miRNAs). The siRNAs then diffuse or are carried throughout the organism, including across cellular membranes, where they hybridize to mRNAs (or other RNAs) and cause hydrolysis of the RNA. Most plant miRNAs show extensive base pairing to, and guide cleavage of their target mRNAs. Jones-Rhoades et al. (2006) *Annu. Rev. Plant Biol.* 57, 19-53; Llave et al. (2002) *Proc. Natl. Acad. Sci. USA* 97, 13401-10406. In other instances, interfering RNAs may bind to target RNA5 molecules having imperfect complementarity, causing translational repression without mRNA degradation.

The mode of action for silencing a plant gene generally includes a double stranded RNA (dsRNA) that associates with a dicer enzyme that cuts the dsRNA into ds fragments 19-24 bps in length (siRNA). There may be more than one dicer enzyme, depending on the organism. Meister and Tuschl, 2004). The siRNA is typically degraded into two single stranded RNAs (ssRNAs), referred to as the passenger strand and the guide strand. A RNA-interference silencing complex (RISC complex) loads the guide strand. The RISC complex associates with a target mRNA that has partial or complete homology to the guide strand. The catalytic RISC component agronaute causes cleavage of the target mRNA preventing it from being used as a translation template. Ahlquist P (2002) *RNA-dependent RNA polymerases, viruses, and RNA silencing*, Science 296 (5571): 1270-3. The RNAi pathway is exploited in plants by using recombinant technology, which entails transforming a plant with a vector comprising DNA that when expressed produces a dsRNA homologous or nearly homologous to a gene target. The gene target can be homologous to a endogenous plant gene or an insect gene. If the target is an insect gene, the insect eats the plant thereby ingesting the dsRNA, at which the RNAi RISC complex of the insect causes cleavage and targeting of the homologous mRNA, causing disruption of a vital insect process.

To date, plant recombinant technology is the vehicle for delivering gene silencing of target genes, either endogenous plant target genes or target genes of a plant pest organism. In general, a plant is transformed with DNA that is incorporated into the plant genome, and when expressed produces a dsRNA that is complementary to a gene of interest, which can be an endogenous plant gene or an essential gene of a plant pest. Plant recombination techniques to generate transgene and beneficial plant traits require significant investments in research and development, and pose significant regulatory hurdles. Methods and formulations for delivering dsRNA into plant cells by exogenous application to exterior portions of the plant, such as leaf, stem, and/or root surfaces for regulation of endogenous gene expression are not known in the art. Such methods and formulations represent a significant development for gene silencing technology.

Known methods for delivering exogenous dsRNA into plant cells are via particle bombardment or viral RNA infection through wounding the plant tissue (e.g. tobacco and rice leaf tissues). Application by spray or brush of RNA molecules, or other non-tissue evasive techniques, resulting in assimilation of the exogenous RNA molecules into plant tissue, thereby causing endogenous and/or pest gene silencing, has not been reported.

The present invention is directed to methods and formulations to incorporate exogenous RNA, by application to external tissue surface(s) of plants, into the plant cells causing silencing of plant endogenous target gene(s) or of the target genes of plant pests.

The present invention is not directed to any particular RNAi mechanism or mode of action of gene silencing, and should not be construed as limited to any such mechanisms, known or unknown.

SUMMARY OF THE INVENTION

This invention disclosure is a novel approach of dsRNA penetration into plant cells and the subsequent induction of plant endogenous gene silencing by application of the dsRNA to a surface of a plant structure, e.g., a leave surface. More significantly, gene silencing was successful in a crop species (maize) rather than model plants (*Arabidopsis* etc).

Thus, the present invention establishes that external application of dsRNA can be used to silence or otherwise modulate endogenous plant gene expression.

This invention disclosure is a novel approach of plant hormone-mediated penetration of dsRNA into plant cells and the subsequent induction of plant endogenous gene silencing by application of the dsRNA to a surface of a plant structure, e.g. a leaf surface. Gene silencing was successful in a crop species (maize) rather than model plants (*Arabidopsis* etc). Thus, the present invention establishes that external application of dsRNA can be used to silence or otherwise modulate endogenous plant gene expression.

This invention disclosure is a novel approach of plant hormone-mediated penetration of dsRNA into plant cells and the subsequent induction of plant endogenous gene silencing by application of the dsRNA in a formulation to a surface of a plant structure, e.g. a leaf surface. Gene silencing was successful in a crop species (maize) rather than model plants (*Arabidopsis* etc). Thus, the present invention establishes that external application of dsRNA can be used to silence or otherwise modulate endogenous plant gene expression.

The invention includes a method of integrating RNA into a plant cell comprising: providing a formulation comprising a gene-specific dsRNA, H2O, and a plant hormone Brassinosteroid and applying the formulation to the leaf surface of a live plant, wherein the RNA is single strand RNA and is assimilated from the external leaf surface into cells of the plant leaf.

It is also understood and it is within the scope of the invention for plant hormones in the formulation and method of the present invention to assist dsRNA processing inside the plant cell for plant endogenous gene silencing.

One aspect of the invention is directed to integrating RNA into a plant cell comprising: providing a formulation comprising a gene-specific dsRNA, H2O, and a plant hormone Brassinosteroid, and applying the formulation to the external surface of a live plant, wherein the dsRNA is assimilated from the external leaf surface into cells of the plant.

One aspect of the invention is directed to integrating RNA into a plant cell comprising: providing a formulation comprising a gene-specific dsRNA, H2O, and a plant hormone Brassinosteroid, and applying the formulation to the external leaf surface of a live plant, wherein the dsRNA is assimilated from the external leaf surface into cells of the plant leaf.

One aspect of the invention is directed to integrating RNA into a plant cell comprising: providing a formulation comprising a gene-specific dsRNA, H2O, and a plant hormone, and applying the formulation to the external surface of a live plant, wherein the dsRNA is assimilated from the external surface into cells of the plant.

Another aspect of the invention includes a formulation including a dsRNA at a concentration of about 250 ng/ul and a Brassinosteroid plant hormone in formulation in range of about 0.8 micromolar to about 1.6 micromolar.

Another aspect of the invention includes using dsRNA in a formulation at a concentration of about 250 ng/ul.

Another aspect of the invention includes using Brassinosteroid plant hormone in formulation in range of about 0.8 micromolar to about 1.6 micromolar.

The invention further includes a formulation comprising a dsRNA, H2O, and a plant hormone to a live plant about 12 days from germination. An aspect of the invention includes applying the formulation to a dicot plant, a maize plant or a tobacco plant.

Another aspect of the invention is a formulation for applying to the external surface of a plant comprising dsRNA, H2O, and a plant hormone Brassinosteroid.

Another aspect of the invention is a wherein the Brassinosteroid in the formulation is at 0.8 micromolar to about 1.6 micromolar.

Yet another aspect of the invention a formulation where the dsRNA in the formulation is at a concentration of about 250 ng/ul.

One aspect of the invention is a method of producing a plant, plant part, or plant cell comprising RNAi for modulating at least one target endogenous gene of the plant.

One aspect of the invention is a method of producing a plant, plant part, or plant cell comprising RNAi for modulating at least one target endogenous gene of the plant.

The present invention includes provides methods and compositions for controlling pest infestation by repressing, delaying, or otherwise reducing gene expression within a particular pest.

BRIEF DESCRIPTION OF THE SEQUENCES

SEQ ID NO 1: depicts 600 nucleotide bases of the ZsGreen gene sequence.

SEQ ID NO 2: depicts 1071 nucleotide bases of the *Zea mays* Glutamine Synthetase cDNA sequence.

SEQ ID NO 3: depicts 395 nucleotide bases of the *Nicotiana tabacum* chloroplast FtsH protease cDNA sequence.

SEQ ID NO 4: depicts 1761 nucleotide bases of the *Nicotiana tabacum* Phytoene Desaturase cDNA sequence SEQ ID NO 5: depicts ssRNA that is sense to SEQ ID NO. 1

SEQ ID NO 6: depicts ssRNA complementary to SEQ ID NO 5.

SEQ ID NO 7: depicts ssRNA sense to SEQ ID NO. 2.

SEQ ID NO 8: depicts ssRNA complementary to SEQ ID NO 7.

SEQ ID NO 9: depicts ssRNA sense to SEQ ID NO. 3

SEQ ID NO 10: depicts ssRNA complementary to SEQ ID NO 9.

SEQ ID NO 11 depicts ssRNA sense to SEQ ID NO 4.

SEQ ID NO 12: depicts ssRNA complementary to SEQ ID NO 11.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety As used herein, "a," "an" or "the" can mean one or more than one. For example, a cell can mean a single cell or a multiplicity of cells.

As used herein, "and/or" refers to and encompasses any and all possible combinations of one or more of the associated listed items, as well as the lack of combinations when interpreted in the alternative (or).

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

The term "RNA" includes any molecule comprising at least one ribonucleotide residue, including those possessing one or more natural ribonucleotides of the following bases: adenine, cytosine, guanine, and uracil; abbreviated A, C, G, and U, respectively, modified ribonucleotides, and non-ribonucleotides. "Ribonucleotide" means a nucleotide with a hydroxyl group at the 2' position of the D-ribofuranose moiety.

As used herein, the terms and phrases "RNA," "RNA molecule(s)," and "RNA sequence(s)," are used interchangeably to refer to RNA that mediates RNA interference. These terms and phrases include single-stranded RNA, double-stranded RNA, isolated RNA, partially purified RNA, essentially pure RNA, synthetic RNA, recombinant RNA, intracellular RNA, and also includes RNA that differs from naturally occurring RNA by the addition, deletion, substitution, and/or alteration of one or more nucleotides of the naturally occurring RNA.

An "interfering RNA" (e.g., siRNA and miRNA) is a RNA molecule capable of post-transcriptional gene silencing or suppression, RNA silencing, and/or decreasing gene expression. Interfering RNAs affect sequence-specific, post-transcriptional gene silencing in animals and plants by base pairing to the mRNA sequence of a target nucleic acid. Thus, the siRNA is at least partially complementary to the silenced gene. The partially complementary siRNA may include one or more mismatches, bulges, internal loops, and/or non-Watson-Crick base pairs (i.e., G-U wobble base pairs).

The terms "silencing" and "suppression" are used interchangeably to generally describe substantial and measurable reductions of the amount of the target mRNA available in the cell for binding and decoding by ribosomes. The transcribed RNA can be in the sense orientation to effect what is referred to as co-suppression, in the anti-sense orientation to effect what is referred to as anti-sense suppression, or in both orientations producing a double-stranded RNA to effect what is referred to as RNA interference. A "silenced" gene includes within its definition a gene that is subject to silencing or suppression of the mRNA encoded by the gene.

MicroRNAs are encoded by genes that are transcribed but not translated into protein (non-coding DNA), although some miRNAs are encoded by sequences that overlap protein-coding genes. By way of background, miRNAs are processed from primary transcripts known as pri-miRNAs to short stem loop structures called pre-miRNAs that are further processed by action of dicer enzyme(s) creating functional siRNAs/miRNAs. Typically, a portion of the precursor miRNA is cleaved to produce the final miRNA molecule. The stem-loop structures may range from, for example, about 50 to about 80 nucleotides, or about 60 nucleotides to about 70 nucleotides (including the miRNA residues, those pairing to the miRNA, and any intervening segments). The secondary structure of the stem-loop structure is not fully base-paired; mismatches, bulges, internal loops, non-WatsonCrick base pairs (i.e., G-U wobble base pairs), and other features are frequently observed in pre-miRNAs and such characteristics are thought to be important for processing. Mature miRNA molecules are partially complementary to one or more mRNA molecules, and they function to regulate gene expression. siRNAs of the present invention have structural and functional properties of endogenous miRNAs (e.g., gene silencing and suppressive functions). Thus, in various aspects of the invention, siRNAs of the invention can derived from miRNAs, from target gene sequence information, or can be produced synthetically based on predictive models known in the art.

The phrases "target-specific small interfering RNAs," "target-specific siRNAs," "target-specific microRNAs," "target-specific miRNAs," "target-specific amiRNAs," and "target-specific nucleotide sequence" refer to interfering RNAs that have been designed to selectively hybridize with nucleic acids in a target organism, but not in a non-target organism, such as a host organism (the organism expressing or producing the miRNA) or a consumer of the host organism. Consequently, "target-specific siRNAs" only produce phenotypes in target organisms and do not produce phenotypes in non-target organisms. In the present invention, the target-specific siRNAs selectively hybridize to nucleic acids that are endogenous to the host organism, which are plants.

MicroRNAs (miRNAs) are non-protein coding RNAs, generally of between about 19 to about 25 nucleotides (commonly about 20-24 nucleotides in plants). miRNAs direct cleavage in trans of target transcripts, regulating the expression of genes involved in various regulation and development pathways (Bartel, *Cell*, 116:281-297 (2004); Zhang et al. *Dev. Biol.* 289:3-16 (2006)). miRNAs have been shown to be involved in different aspects of plant growth and development as well as in signal transduction and protein degradation. In addition, growing evidence indicates that small endogenous mRNAs including miRNAs may also be involved in biotic stress responses such as parasite attack. Since the first miRNAs were discovered in plants (Reinhart et al. *Genes Dev.* 16:1616-1626 (2002), Park et al. *Curr. Biol.* 12:1484-1495 (2002)), many hundreds have been identified. Further, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database ("miR-Base," available on line at microrna.sanger.ac.uk/sequences). miRNAs are also described in U.S. Patent Publications 2005/0120415 and 2005/144669A1, the entire contents of which are incorporated by reference herein.

As used herein, "heterologous" refers to a nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, and/or under the control of different regulatory sequences than that found naturally in nature.

The terms "increase," "increased," "enhance," "enhanced," "enhancing," and "enhancement" (and grammatical variations thereof), as used herein, describe an increase in the resistance of a plant to a parasite (e.g., a soybean plant having increased resistance to the soybean cyst nematode) by the introduction of a heterologous miRNA nucleotide sequence of the present invention into the plant, thereby producing a transgenic plant having increased resistance to the parasite. This increase can be observed by comparing the resistance of the plant transformed with the heterologous miRNA nucleotide sequence of the invention to a plant (e.g., soybean) that is not transformed with the heterologous miRNA nucleotide sequence of the invention (e.g., a soybean plant transformed with the heterologous miR164 nucleotide sequence compared to a soybean plant that is not transformed with the heterologous miR164 nucleotide sequence).

As used herein, the term "nucleic acid," "nucleic acid molecule," and/or "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the sequence rules for the U.S. Patent and Trademark Office, 37 CFR §§1.821-1.825, and the World Intellectual Property Organization (WIPO) Standard ST.25.

As used herein, the term "gene" refers to a nucleic acid molecule capable of being used to produce mRNA, anti-sense RNA, miRNA, and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

The term "nucleic acid fragment" will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of and/or consist of, oligonucleotides having a length of at least about 6, 7, 8, 9, 10, 11, 12, 13, 14, 15, 16, 17, 18, 19, 20, 21, 22, 23, 24, 25, 50, 75, 100, 150, 200, 250, 300, 350, 400, 450, 500, 750, or 1000 consecutive nucleotides of a nucleic acid or nucleotide sequence according to the invention.

An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous).

Thus, an "isolated nucleic acid" is present in a form or setting that is different from that in which it is found in nature and is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. Thus, a nucleic acid found in nature that is removed from its native environment and transformed into a plant is still considered "isolated" even when incorporated into the genome of the resulting transgenic plant. It also includes a recombinant nucleic acid that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. As used herein, the terms "protein" and "polypeptide" are used interchangeably and encompass peptides, unless indicated otherwise. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. A fragment of a polypeptide or protein can be produced by methods well known and routine in the art, for example, by enzymatic or other cleavage of naturally occurring peptides or polypeptides or by synthetic protocols that are well known.

A polypeptide fragment can be a biologically active fragment. A "biologically active fragment" or "active fragment" refers to a fragment that retains one or more of the biological activities of the reference polypeptide. Such fragments can be tested for biological activities according to methods described in the art, which are routine methods for testing activities of polypeptides, and/or according to any art-known and routine methods for identifying such activities. The production and testing to identify biologically active fragments of a polypeptide would be well within the scope of one of ordinary skill in the art and would be routine. Thus, the present invention further provides biologically active fragments of a polypeptide such as a polypeptide of interest and the polynucleotides encoding such biologically active polypeptide fragments.

The term "transgene" as used herein, refers to any nucleic acid sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism.

Different nucleic acids or polypeptides having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity"

may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J. Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo, H., and Lipton, D., (*Applied Math* 48:1073 (1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

Accordingly, the present invention further provides nucleotide sequences having significant sequence identity to the nucleotide sequences of the present invention. Significant sequence similarity or identity means at least 70%, 75%, 80%, 81%, 82%, 83%, 84%, 85%, 86%, 87%, 88%, 89%, 90%, 91%, 92%, 93%, 94%, 96%, 97%, 98%, 99% and/or 100% similarity or identity with another nucleotide sequence.

"Introducing," in the context of a nucleotide sequence of interest (e.g., miR164), means presenting the nucleotide sequence of interest to the plant, plant part, and/or plant cell in such a manner that the nucleotide sequence gains access to the interior of a cell. Where more than one nucleotide sequence is to be introduced these nucleotide sequences can be assembled as part of a single polynucleotide or nucleic acid construct, or as separate polynucleotide or nucleic acid constructs, and can be located on the same or different transformation vectors. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient.

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

The terms "reduce," "reduced," "reducing," "reduction," "diminish," and "decrease" (and grammatical variations thereof), as used herein, describe a decrease in the soybean cyst nematode cyst formation on a plant (e.g., soybean) by the introduction of a miRNA of the present invention into the plant, thereby producing a transgenic plant having decreased or reduced cyst formation on the transgenic plant. This decrease in cyst formation can be observed, by comparing the number of cysts formed on the plant transformed with the heterologous miR164 nucleotide sequence to the number formed on a soybean plant that is not transformed with the heterologous miR164 nucleotide sequence.

By "stably introducing" or "stably introduced" in the context of a polynucleotide introduced into a cell is intended the introduced polynucleotide is stably incorporated into the genome of the cell, and thus the cell is stably transformed with the polynucleotide. "Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A nucleic acid (e.g., ZsGreen) can be introduced into a cell by any method known to those of skill in the art. In some embodiments of the present invention, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Mild et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

Example 1

Silencing of ZsGreen in Transgenic Maize Plants

ZsGreen-transgenic maize vector 15779 was created and is shown in Figure 1. The ZsGreen fluorescent protein is more fully described in a publication entitled: *Reef-Coral proteins as visual, non-destructive reporters for plant transformation*. Plant Cell Rep (2003) 22:244-251. The vector was transformed into disarmed *Agrobacterium tumafaciens* strain LBA4404 containing helper plasmid pSB1.

dsRNA was generated from known ZsGreen sequence. Various lengths of dsRNA derived from a target gene may be used according to the invention. By way of example only, the following sequence was used in the formulation of the invention. This sequence is a dsRNA version (SEQ ID NO 5:SEQ ID NO 6) of DNA coding SEQ ID NO 1:

```
5'
AGGGCUGCGUGGACGGCCACAAGUUCGUGAUCACCGGCGAGGGCAUCGGCUACCCCUUCAAGGGCAAGCA
|||||||||||||||||||||||||||||||||||||||||||||||||||||||||||||||||||||
UCCCGACGCACCUGCCGGUGUUCAAGCACUAGUGGCCGCUCCCGUAGCCGAUGGGGAAGUUCCCGUUCGU
                                                                    3'

GGCCAUCAACCUGUGCGUGGUGGAGGGCGGCCCCUUGCCCUUCGCCGAGGACAUCUUGUCCGCCGCCUUC
|||||||||||||||||||||||||||||||||||||||||||||||||||||||||||||||||||||
CCGGUAGUUGGACACGCACCACCUCCCGCCGGGGAACGGGAAGCGGCUCCUGUAGAACAGGCGGCGGAAG
```

-continued
```
AUGUACGGCAACCGCGUGUUCACCGAGUACCCCCAGGACAUCGUCGACUACUUCAAGAACUCCUGCCCCG
|||||||||||||||||||||||||||||||||||||||||||||||||||||||||||||||||||||
UACAUGCCGUUGGCGCACAAGUGGCUCAUGGGGGUCCUGUAGCAGCUGAUGAAGUUCUUGAGGACGGGGC CCGGCUACACCUGGGACCGCUCCUUCCUGUUCGAGGACGGCGCCGUGUGCAUCUGCAACGCCGACAUCAC
|||||||||||||||||||||||||||||||||||||||||||||||||||||||||||||||||||||
GGCCGAUGUGGACCCUGGCGAGGAAGGACAAGCUCCUGCCGCGGCACACGUAGACGUUGCGGCUGUAGUG CGUGAGCGUGGAGGAGAACUGCAUGUACCACGAGUCCAAGUUCUACGGCGUGAACUUCCCCGCCGACGGC
|||||||||||||||||||||||||||||||||||||||||||||||||||||||||||||||||||||
GCACUCGCACCUCCUCUUGACGUACAUGGUGCUCAGGUUCAAGUAGCCGCACUUGAAGGGGCGGCUGCCG CCCGUGAUGAAGAAGAUGACCGACAACUGGGAGCCCUCCUGCGAGAAGAUCAUCCCCGUGCCCAAGCAGG
|||||||||||||||||||||||||||||||||||||||||||||||||||||||||||||||||||||
GGGCACUACUUCUUCUACUGGCUGUUGACCCUCGGGAGGACGCUCUUCUAGUAGGGGCACGGGUUCGUCC GCAUCUUGAAGGGCGACGUGAGCAUGUACCUGCUGCUGAAGGACGGUGGCCGCUUGCGCUGCCAGUUCGA
|||||||||||||||||||||||||||||||||||||||||||||||||||||||||||||||||||||
CGUAGAACUUCCCGCUGCACUCGUACAUGGACGACGACUUCCUGCCACCGGCGAACGCGACGGUCAAGCU CACCGUGUACAAGGCCAAGUCCGUGCCCCGCAAGAUGCCCGACUGGCACUUCAUCCAGCACAAGCUGACC
|||||||||||||||||||||||||||||||||||||||||||||||||||||||||||||||||||||
GUGGCACAUGUUCCGGUUCAGGCACGGGCGUUCUACGGGCUGACCGUGAAGUAGGUCGUGUUCGACUGG 3'
CGCGAGGACCGCAGCGACGCCAAGAACCAGAAGUGGCACC
||||||||||||||||||||||||||||||||||||||||
GCGCUCCUGGCGUCGCUGCGGUUCUUGGUCUUCACCGUGG
                                        5'
```

The dsRNA formulation (dsRNA treatment) included about 250 ng/ul dsRNA, H2O, and a plant hormone brassinosteroid (BR) at about 0.8 micromolar to about 1.6 micromolar. The control solution was the same solution, absent ZsGreen dsRNA.

In one embodiment, the Brassinosteroid used in the formulation of the invention is an Epibrassinolide (22R, 23R, 24R-2a, 3a, 22, 23-Tetrahydrosy-B-homo-7-oxa-5a-ergostan-6-one (PubChem Substance ID: 24894426).

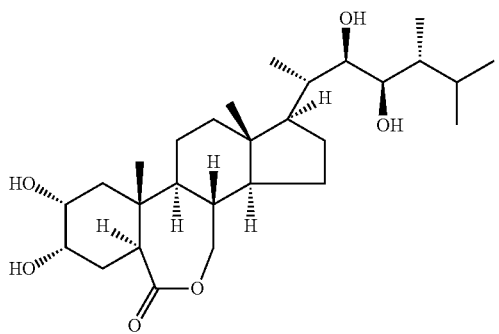

It is within the scope of the present invention to use any plant hormone in the formulation and method of the present, provided it is capable of mediating penetration of dsRNA into plant cells and the subsequent induction of plant endogenous gene silencing by application of the formulation to a surface of a plant structure.

It is also within the scope of the present invention to use a combination of two or more plant hormones in the formulation and method of the present invention, provided the combination is capable of mediating penetration of dsRNA into plant cells and the subsequent induction of plant endogenous gene silencing by application of the formulation to a surface of a plant structure.

It is also understood and it is within the scope of the invention that the plant hormone in the formulation or the combination of plant hormones in the formulation and method of the present invention may assist dsRNA processing inside the plant cell for plant endogenous gene silencing. Other plant hormones that could be used according to the method of the present invention include abscisic acid, auxins, cytokinins, gibberellins, jasmonates, ethylene, salicyclic acid, nitric oxide, or strigolactones.

Seeds transformed with binary vector 15760 and shown to express ZsGreen were germinated at 25 C in darkness for 12 days. Once germinated, 4 plants were chosen as control group, and 4 plants as dsRNA treatment group. At around 12 days after germination, the control or dsRNA formulated solution was dripped onto the maize leaf surface. Leakage of the solution from the leaf to root was prevented by wrapping layers of parafilm at the junction part between leaf and stem. ZsGreen fluorescence in the plant leaves was visualized under UV light and was recorded at various time points post-treatment. Silencing was observed as early as 9 days post-treatment. Evaluation of ZsGreen silencing was based on the comparison of green fluorescence between control and dsRNA treated plant leaves. At 20 days post-treatment, ZsGreen silencing in four dsRNA treatment plants were observed under a Zeiss dissecting microscope at 3-4× magnification; this magnification is capable of detecting the silencing phenomena at the cellular level in leaf tissue.

ZsGreen expression was detected in the leaf tissue of the four control plants, demonstrating that silencing of ZsGreen expression did not occur in the control plants. One control plant, however, was contaminated by fungus and the plantlet did not have strong green fluorescence.

In all four plants that were treated with the dsRNA formulation as described above, the expression of the ZsGreen was silenced. The green-fluorescence signal of the treated plant leaves was not detectable under UV light at the same fixed exposure time as in the control group, demonstrating the severe silencing phenotype.

Overall, the data established high efficacy of silencing (100% in treatment vs % in control), demonstrating the efficacy of spraying dsRNA for regulating endogenous gene expression in crop plants.

Example 2

Silencing of Maize Glutamine Synthetase

A similar experiment was performed using dsRNA generated from the known maize glutamine synthetase RNA sequence Zma-GS dsRNA was synthesized using the AmpliScribe™ T7-Flash™ Transcription Kit, Epicentre® (an Illumina Company) according to manufacturer's suggested protocol. The Zma-GS dsRNA molecule (SEQ ID NO 7:SEQ ID NO 8) used in this embodiment is a double stranded RNA version of SEQ ID NO 2. Methods for formulation of dsRNA and control solutions, plant growth conditions, and application of RNAi formulation were as described in the above example, with the exception that another control formulation was added with only Brassinosteroid at 0.1 micromolar.

Results were evaluated from leaf samples taken 2-3 weeks after treatment. Four plants were examined from each treatment group. Phenotypically, bleaching was observed on the dsRNA treated plants. Since glutamine synthetase is a natively expressed gene, qPCR analysis was performed to calculate silencing efficiency. qPCR was performed using the Applied Biosystems 7900HT Fast Real-Time PCR System. Silencing efficiency was calculated according to the publication *Analysis of Relative Gene Expression Data Using Real-Time Quantitative PCR and the $2^{-\Delta\Delta Ct}$ Method*. Methods (2001) 25:402-408. Briefly, $\Delta C_t$ was calculated for each sample, where $\Delta C_t$=sample $C_t$-reference $C_t$; $\Delta\Delta C_t$=experimental$\Delta C_t$-control$\Delta C_t$; silencing efficiency= $(1-2^{-\Delta\Delta Ct})\times 100\%$ The following table displays the results, where "dsGS" is the Zma-GS dsRNA described above:

| Event | Formulation | Silencing Efficiency |
| --- | --- | --- |
| ZmGS-Tt-1 | dsGS + BR + H2O | 84.07% |
| ZmGS-Tt-2 | dsGS + BR + H2O | 73.37% |
| ZmGS-Tt-3 | dsGS + BR + H2O | 86.64% |
| ZmGS-Tt-4 | dsGS + BR + H2O | 81.99% |
| ZmGS-CK-1-1 | dsGS + H2O | 11.71% |
| ZmGS-CK-1-2 | dsGS + H2O | 0% |
| ZmGS-CK-1-3 | dsGS + H2O | 12.78% |
| ZmGS-CK-1-4 | dsGS + H2O | 0% |
| ZmGS-CK-2_1 | BR + H2O | 0% |
| ZmGS-CK-2_2 | BR + H2O | 0% |
| ZmGS-CK-2_3 | BR + H2O | 12.21% |
| ZmGS-CK-2_4 | BR + H2O | 0% |

Example 3

Silencing of NtFtsH Transcript in Tobacco

The tobacco gene encoding Filamentation temperature-sensitive H (NtFtsH) protease was evaluated for silencing using dsRNA constructs in combination with BR. Tobacco was chosen as a model dicot plant system, and these experiments demonstrate that this approach is valid in dicotyledenous species as well. Similar to Example 2, dsRNA was synthesized using AmpliScribe™ T7-Flash™ Transcription Kit, Epicentre® (an Illumina Company) according to manufacturer's suggested protocol. The NtFtsH protease dsRNA molecule (SEQ ID NO 9:SEQ ID NO 10) used in this embodiment is a double stranded version of SEQ ID NO. 3.

Once germinated, tobacco plants were transplanted to new soil and grown for an additional 3-4 weeks. Three tobacco plants were chosen for treatment for either the dsRNA or the control formulation. The treatments were applied using methods similar to those described in Example 2. Here, the control formulation contained ZsGreen dsRNA. The tobacco plants did not have the ZsGreen transgene. Similar to Example 2, a bleaching phenotype was observed in the leaves of the dsRNA treated plants, and results were evaluated by performing qPCR on samples taken 2-3 weeks after treatment. As in Example 2, the silencing efficiencies were calculated and are shown in the table below, where dsNtFtsH is dsRNA from NtFtsH protease and dsZsGreen is the dsRNA of ZsGreen:

| Event | Formulation | Silencing Efficiency |
| --- | --- | --- |
| Spray NtFtsH_1 | dsNtFtsH + BR + H2O | 73.49% |
| Spray NtFtsH_2 | dsNtFtsH + BR + H2O | 82.21% |
| Spray NtFtsH_3 | dsNtFtsH + BR + H2O | 77.22% |
| CK Spray-1 | dsZsGreen + BR + H2O | 0% |
| CK Spray-1 | dsZsGreen + BR + H2O | 0% |
| CK Spray-1 | dsZsGreen + BR + H2O | 0% |

Example 4

Silencing of NtPDS Transcript in Tobacco

The tobacco gene encoding phytoene desaturase was evaluated for silencing using dsRNA constructs in combination with BR. Similar to Example 2 and 3, dsRNA was synthesized using AmpliScribe™ T7-Flash™ Transcription Kit, Epicentre® (an Illumina Company) according to manufacturer's suggested protocol. The NtPDS dsRNA molecule (SEQ ID NO 10:SEQ ID NO 11) used in this embodiment is a double stranded RNA version of SEQ ID NO 4.

Similar to Example 3, once germinated and grown for 3-4 weeks, three tobacco plants were chosen for treatment for either the dsRNA or the control formulation. Here, the control formulation contained BR and water alone. Similar to Examples 2 and 3, a bleaching phenotype was observed in the leaves of the dsRNA treated plants, and results were evaluated by performing qPCR on samples taken 2-3 weeks after treatment. As in Examples 2 and 3, the silencing efficiencies were calculated and are shown in the table below, where dsPDS is dsRNA from NtPDS.

| Event | Formulation | Silencing Efficiency |
| --- | --- | --- |
| Spray_NtPDS-1 | dsPDS + BR + H2O | 75.58% |
| Spray_NtPDS-2 | dsPDS + BR + H2O | 85.55% |
| Spray_NtPDS-3 | dsPDS + BR + H2O | 67.42% |
| Spray_NtPDS-CK-1 | BR + H2O | 0% |
| Spray_NtPDS-CK-2 | BR + H2O | 0% |
| Spray_NtPDS-CK-3 | BR + H2O | 0% |

Overall, these examples demonstrate that application of dsRNA formulations with a plant hormone has silencing effects on both monocotyledonous and dicotyledonous plant cells. In one embodiment, the plant hormone may be a brassinosteroid.

The present invention, therefore, demonstrates the ability to introduce dsRNA into plant cells by application of a formulation to a plant surface and to then silence gene protein expression therein.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the list of the foregoing embodiments and the appended claims.

What is claimed is:

1. A method of integrating dsRNA into a plant cell to silence an endogenous target gene of a plant comprising:
   a) providing a formulation comprising a gene-specific dsRNA, water, and a plant hormone Brassinosteroid, wherein the Brassinosteroid is at 1.0 micromolar, and wherein the gene-specific dsRNA is derived from the endogenous target gene encoding a glutamine synthetase;
   b) applying the formulation to the leaf surface of a live plant, wherein the dsRNA is assimilated from the external leaf surface into cells of the plant leaf, wherein the silencing efficiency of the endogenous target gene is increased five to eight fold compared to a formulation containing the dsRNA without the plant hormone Brassinosteroid, and wherein the plant is a maize plant.

2. The method of claim 1 wherein the step of applying the formulation is to a live plant about 12 days from germination.

3. The method of claim 1 wherein the gene-specific dsRNA is derived from the glutamine synthetase cDNA sequence depicted in SEQ ID NO: 2.

4. A method of integrating dsRNA into a plant cell to silence an endogenous target gene of a plant comprising:
   a) providing a formulation comprising a gene-specific dsRNA, water, and a plant hormone Brassinosteroid, wherein the dsRNA is at about 250 nanograms per microliter, wherein the Brassinosteroid is at 1.0 micromolar, and wherein the gene specific dsRNA is derived from the endogenous target gene encoding a glutamine synthetase; and
   b) applying the formulation to the leaf surface of a live plant, wherein the dsRNA is assimilated from the external leaf surface into cells of the plant leaf, wherein the silencing efficiency of the endogenous target gene is increased five to eight fold compared to a formulation containing the dsRNA without the plant hormone Brassinosteroid, and wherein the plant is a maize plant.

5. The method of claim 4 wherein the step of applying the formulation is to a live plant about 12 days from germination.

6. The method of claim 4 wherein the gene-specific dsRNA is derived from the glutamine synthetase cDNA sequence depicted in SEQ ID NO: 2.

7. A method of integrating dsRNA into a plant cell to silence an endogenous target gene of a plant comprising:
   a) providing a formulation comprising a gene-specific dsRNA, water, and a plant hormone Brassinosteroid, wherein the Brassinosteroid is at 1.0 micromolar, and wherein the gene-specific dsRNA is derived from the glutamine synthetase cDNA sequence depicted in SEQ ID NO: 2; and
   b) applying the formulation to the leaf surface of a live plant about 12 days from germination, wherein the dsRNA is assimilated from the external leaf surface into cells of the plant leaf, wherein the silencing efficiency of the endogenous target gene is increased five to eight fold compared to a formulation containing the dsRNA without the plant hormone Brassinosteroid, and wherein the plant is a maize plant.

* * * * *